United States Patent [19]

Vlasblom

[11] Patent Number: 5,565,208
[45] Date of Patent: Oct. 15, 1996

[54] INSECT REPELLENT AEROSOL

[75] Inventor: Jack T. Vlasblom, Dunedin, Fla.

[73] Assignee: Citra Science Ltd., Largo, Fla.

[21] Appl. No.: 333,641

[22] Filed: Nov. 3, 1994

[51] Int. Cl.$^6$ ........................................... A61K 9/12
[52] U.S. Cl. ............................................. 424/405; 424/45
[58] Field of Search ............................. 424/405, 43, 45

[56] References Cited

U.S. PATENT DOCUMENTS 5,136,136  7/1992  Shono et al. ............................ 424/405

OTHER PUBLICATIONS

Fibre, World Patent Abstract of WO 8903639.

Otsuka, World Patent Abstract of JP 01197404.

Allan et al., *Chemical Abstracts*, vol. 106, #115267S, 1986.

*Primary Examiner*—Thurman K. Page
*Assistant Examiner*—P. Webber
*Attorney, Agent, or Firm*—Donald R. Fraser

[57] ABSTRACT

An insect repellent having extended repellency consists of d-limonene, di-N-propyl isocinchomeronate, N-octyl bicycloheptene dicarboximide, C-11 alcohol ethoxylate, polysorbate 80, and an organic solvent selected from the group consisting of dipropylene glycol N-butyl ether, citronella oil, dimethyl phthalate, and N,N-diethyl-m-toluamide, and mixtures thereof.

21 Claims, No Drawings

INSECT REPELLENT AEROSOL

FIELD OF THE INVENTION

This invention relates generally to an insect repellent. More particularly, the invention is directed to an insect repellent formulation containing, inter alia, d-limonene, which insect repellent is useful as a concentrate or aqueous mixture for application to humans and animals to repel insects.

BACKGROUND OF THE INVENTION

Insect repellent formulations are well-known for providing temporary repellency for insects. Such formulations are generally applied to the skin of humans or the coats of animals to provide repellency which lasts a few hours. Extended repellency is difficult to achieve utilizing the known combinations of conventional repellent chemical compounds.

It would be desirable to prepare an insect repellent formulation having extended repellency of up to two days from the time of application, which repellent formulation is aesthetically pleasing to the senses having a citrus or sweet bouquet.

SUMMARY OF THE INVENTION

Accordant with the present invention, an extended repellency insect repellent has surprisingly been discovered. It consists of d-limonene, di-N-propyl isocinchomeronate, N-octyl bicycloheptene dicarboximide, C-11 alcohol ethoxylate, Polysorbate 80, and an organic solvent selected from the group consisting of dipropylene glycol N-butyl ether, citronella oil, dimethyl phthalate, and N,N-diethyl-m-toluamide, as well as mixtures thereof.

The insect repellent formulation of the present invention is particularly useful for applying directly or as an aqueous solution to the skin of humans or the coats of animals to repel insects therefrom.

DETAILED DESCRIPTION OF THE PREFERRED EMBODIMENTS

The insect repellent formulation according to the present invention consists of a precise combination of d-limonene, di-N-propyl isocinchomeronate, N-octyl bicycloheptene dicarboximide, C-11 alcohol ethoxylate, polysorbate 80, and an organic solvent selected from the group consisting of dipropylene glycol N-butyl ether, citronella oil, dimethyl phthalate, and N,N-diethyl-m-toluamide, as well as mixtures thereof.

D-limonene is a terpene which occurs naturally in all living plants. It is a monocyclic unsaturated terpene which is generally a by product of the citrus industry, derived from the distilled rind oils of oranges, grapefruits, lemons, and the like. A discussion of d-limonene and its derivation from numerous sources is set forth in Kesterson, J. W., "Florida Citrus Oil," Institute of Food and Agricultural Sciences, University of Florida, December, 1971. D-limonene is commercially available from Florida Chemical Company and SMC Glidco Organics. D-limonene may be present in the inventive formulation at a concentration from about 15 to about 70 weight percent. Preferably, the concentration of d-limonene ranges from about 35 to about 50 weight percent.

The inventive insect repellent formulation contains di-N-propyl isocinchomeronate, a known insect repelling chemical compound. The di-N-propyl isocinchomeronate may be present in the formulation at a concentration from about 5 to about 38 weight percent. Preferably, the concentration is about 10 weight percent. A preferred di-N-propyl isocinchomeronate is available from McLaughlin Gormley King Co. of Minneapolis, Minn. under the product designation "R-326".

N-octyl bicycloheptene dicarboximide is contained in the formulation as a synergist and activator for the di-N-propyl isocinchomeronate. It may be present at a concentration from about 4 to about 38 weight percent. Preferably, the concentration is about 10 weight percent. A preferred N-octyl bicycloheptene dicarboximide is available from McLaughlin Gormley King Co. of Minneapolis, Minn. under the product designation "K-264".

C-11 alcohol ethoxylate is present in the repellent formulation as an emulsifier. The concentration of C-11 alcohol ethoxylate may range from about 5 to about 38 weight percent. Preferably, the concentration is about 10 weight percent. A preferred C-11 alcohol ethoxylate may be obtained from Van Waters & Rogers, Inc. of Kirkland, Wash. under the product designation "NEODOL 1-5".

The inventive formulation contains polysorbate 80 as a surfactant and dispersing agent. It may be present at a concentration from about 4 to about 38 weight percent. Preferably, the concentration is about 10 weight percent.

The inventive repellent additionally contains an organic solvent selected from the group consisting of dipropylene glycol N-butyl ether, citronella oil, dimethyl phthalate, and N,N-diethyl-m-toluamide, as well as mixtures thereof. The solvent may be present at a concentration from about 5 to about 59 weight percent. Preferably, the organic solvent concentration ranges from about 10 to about 25 weight percent. These organic solvents are well-known in the insect repellent chemical arts.

The ingredients are combined and mixed together in conventional mixing apparatus, to prepare a sprayable liquid insect repellent which may be applied directly to the skin of humans or the coats of animals, to repel insects therefrom for up to two full days. Alternatively the formulation may be mixed with up to about fifty parts by weight water to form an aqueous solution that can be atomized by conventional fogging equipment, to effectively repel insects from an enclosure such as a barn or an outdoor area. Conveniently, the insect repellent formulations according to the present invention display a citrus or sweet odor which is aesthetically pleasing to the user.

EXAMPLES

The following ingredients are mixed together in the approximate weight percentages indicated, to form a sprayable liquid insect repellent. The resultant formulations are then applied to the skin of humans or coats of animals to provide insect repellency for up to two full days.

TABLE I

| REPELLENT FORMULATIONS | | | | |
|---|---|---|---|---|
| Ingredient | Ex. 1 | Ex. 2 | Ex. 3 | Ex. 4 |
| d-limonmene (1) | 50 | 50 | 50 | 35 |
| di-N-propyl | 10 | 10 | 10 | 10 |

TABLE I-continued

REPELLENT FORMULATIONS

| Ingredient | Ex. 1 | Ex. 2 | Ex. 3 | Ex. 4 |
|---|---|---|---|---|
| isocinchomeronate (2) | | | | |
| N-octyl bicycloheptene dicarboximide (3) | 10 | 10 | 10 | 10 |
| C-11 alcohol ethoxylate (4) | 10 | 10 | 10 | 10 |
| polysorbate 80 | 10 | 10 | 10 | 10 |
| dipropylene glycol N-butyl ether | 10 | | | |
| citronella oil | | 10 | | |
| dimethyl phthalate | | | 10 | |
| N,N-diethyl-m-toluamide | | | | 25 |

(1) GLIDSAFE, from SMC Glidco Organics
(2) R-326, from McLaughlin Gormley King Co.
(3) K-264, From McLaughlin Gormley King Co.
(4) NEODOL 1-5, from Van Waters & Rogers Inc.

These Examples may be repeated with similar success by substituting the generically or specifically described ingredients and/or concentrations recited herein for those set forth in the preceding Examples.

From the foregoing description, one ordinarily skilled in the art can easily ascertain the essential characteristics of this invention and, without departing from its spirit or scope, can make various changes and modifications in the invention to adapt it to various usages and conditions.

What is claimed is:

1. An insect repellent, consisting of:
   d-limonene;
   di-N-propyl isocinchomeronate;
   N-octyl bicycloheptene dicarboximide;
   C-11 alcohol ethoxylate;
   polysorbate 80; and
   an organic solvent selected from the group consisting of dipropylene glycol N-butyl ether, citronella oil, dimethyl phthalate, and N,N-diethyl-m-toluamide, as well as mixtures thereof.

2. The insect repellent according to claim 1, wherein the concentration of d-limonene ranges from about 15 to about 70 weight percent.

3. The insect repellent according to claim 2, wherein the d-limonene concentration ranges from about 35 to about 50 weight percent.

4. The insect repellent according to claim 1, wherein the concentration of di-N-propyl isocinchomeronate ranges from about 5 to about 38 weight percent.

5. The insect repellent according to claim 4, wherein the di-N-propyl isocinchomeronate concentration is about 10 weight percent.

6. The insect repellent according to claim 1, wherein the concentration of N-octyl bicycloheptene dicarboximide ranges from about 4 to about 38 weight percent.

7. The insect repellent according to claim 6, wherein the N-octyl bicycloheptene dicarboximide concentration is about 10 weight percent.

8. The insect repellent according to claim 1, wherein the concentration of C-11 alcohol ethoxylate ranges from about 5 to about 38 weight percent.

9. The insect repellent according to claim 8, wherein the C-11 alcohol ethoxylate concentration is about 10 weight percent.

10. The insect repellent according to claim 1, wherein the concentration of polysorbate 80 ranges from about 4 to about 38 weight percent.

11. The insect repellent according to claim 10, wherein the polysorbate 80 concentration is about 10 weight percent.

12. The insect repellent according to claim 1, wherein the concentration of organic solvent ranges from about 5 to about 59 weight percent.

13. The insect repellent according to claim 12, wherein the organic solvent concentration ranges from about 10 to about 25 weight percent.

14. An insect repellent, consisting of:
   from about 15 to about 70 weight percent d-limonene;
   from about 5 to about 38 weight percent di-N-propyl isocinchomeronate;
   from about 4 to about 38 weight percent N-octyl bicycloheptene dicarboximide;
   from about 5 to about 38 weight percent C-11 alcohol ethoxylate;
   from about 4 to about 38 weight percent polysorbate 80; and
   from about 5 to about 59 weight percent organic solvent selected from the group consisting of dipropylene glycol N-butyl ether, citronella oil, dimethyl phthalate, and N,N-diethyl-m-toluamide, as well as mixtures thereof.

15. The insect repellent according to claim 14, wherein the d-limonene concentration ranges from about 35 to about 50 weight percent.

16. The insect repellent according to claim 14, wherein the di-N-propyl isocinchomeronate concentration is about 10 weight percent.

17. The insect repellent according to claim 14, wherein the N-octyl bicycloheptene dicarboximide concentration is about 10 weight percent.

18. The insect repellent according to claim 14, wherein the C-11 alcohol ethoxylate concentration is about 10 weight percent.

19. The insect repellent according to claim 14, wherein the polysorbate 80 concentration is about 10 weight percent.

20. The insect repellent according to claim 14, wherein the organic solvent concentration ranges from about 10 to about 25 weight percent.

21. An insect repellent, consisting of:
   from about 35 to about 50 weight percent d-limonene;
   about 10 weight percent di-N-propyl isocinchomeronate;
   about 10 weight percent N-octyl bicycloheptene dicarboximide;
   about 10 weight percent C-11 alcohol ethoxylate;
   about 10 weight percent polysorbate 80; and
   from about 10 to about 25 weight percent organic solvent selected from the group consisting of dipropylene glycol N-butyl ether, citronella oil, dimethyl phthalate, and N,N-diethyl-m-toluamide, as well as mixtures thereof.

* * * * *